United States Patent [19]

Northeimer, deceased

[11] 3,959,383

[45] May 25, 1976

[54] TWO-STAGE CONVERSON OF METHANOL TO FORMALDEHYDE

[75] Inventor: Evan S. Northeimer, deceased, late of Charleston, W. Va., by Margaret Northeimer, executrix

[73] Assignee: E. I. Du Pont de Nemours and Company, Wilmington, Del.

[22] Filed: Mar. 7, 1974

[21] Appl. No.: 448,994

Related U.S. Application Data

[63] Continuation-in-part of Ser. No. 742,989, April 16, 1968, which is a continuation-in-part of Ser. No. 465,975, June 22, 1965, abandoned.

[52] U.S. Cl................................. 260/603 C
[51] Int. Cl.$^2$............................... C07C 45/16
[58] Field of Search........................ 260/603 C

[56] References Cited
UNITED STATES PATENTS

| | | |
|---|---|---|
| 1,968,552 | 7/1934 | Bond................................. 260/603 |
| 2,462,413 | 2/1949 | Meath................................ 260/603 |
| 2,519,788 | 8/1950 | Payne................................ 260/603 |
| 2,908,715 | 10/1959 | Eguchi................................ 260/603 |

Primary Examiner—James O. Thomas
Assistant Examiner—James H. Reamer

[57] ABSTRACT

A two-stage conversion of methanol to formaldehyde characterized in that silver crystals having a size range of 8 to 40 screen mesh are employed as a catalyst in the second stage converter and space velocity in said converter is maintained within a range of from 250,000 to 600,000 reciprocal hours. The process yields a high strength formaldehyde product containing small amounts of methanol.

3 Claims, No Drawings

TWO-STAGE CONVERSION OF METHANOL TO FORMALDEHYDE

CROSS-REFERENCE TO RELATED APPLICATIONS

This application is a continuation-in-part of my co-pending application Ser. No. 742,989, filed Apr. 16, 1968, which application was a continuation-in-part of my copending application Ser. No. 465,975, filed June 22, 1965, now abandoned.

BACKGROUND OF THE INVENTION

Meath U.S. Pat. No. 2,462,413 discloses a scheme for the production of formaldehyde involving the oxidation of air-methanol mixtures in a two-stage conversion process with interstage cooling. While such a process is successful in controlling the temperature of reaction during oxidation and thereby minimizing decomposition of formaldehyde and product formed, it offers as a disadvantage a relatively high leakage of unconverted methanol. This makes it difficult to operate such a process to manufacture high strength aqueous formaldehyde solutions, such as 60% formaldehyde, containing less than 2% methanol.

It has been found in accordance with the present invention that such a two-stage conversion process yielding a high strength formaldehyde product containing low concentrations of methanol can be obtained by use of significantly higher space velocities in the second stage converter, together with the use of a silver catalyst in a specified form and size.

SUMMARY OF THE INVENTION

This invention is related to an improved two-stage oxidation of methanol to formaldehyde employing in the second stage high space velocity and a silver catalyst of critical form and size. The space velocity in the second stage converter is maintained above 250,000 and preferably within a range of from 250,000 to 600,000 reciprocal hours (volume of gas per volume of catalyst per hour). The silver catalyst for use in the second stage of the process is in the form of crystals having a particle size range of from 8 to 40 mesh U.S. screen size (this means particles passing through 8 mesh screen but retained on 40 mesh screen). Particularly preferred for the purposes of the invention are silver crystals having a particle size of from 20 to 30 screen size (U.S. screen size). The silver crystals for use in the process hereof are prepared preferably by electrolytical deposition from a bath of silver nitrate solution. The improved process of the invention conveniently provides for the preparation of 60% by weight aqueous formaldehyde solution containing less than 2% by weight methanol.

DETAILED DESCRIPTION OF THE INVENTION

In executing the improved process of the invention, a feed mix of methanol and air is passed into a primary converter containing silver catalyst and reacted at an adiabatic temperature in the range of about 575°C. to about 650°C. The silver catalyst in this primary converter may be in the form of silver gauze or silver crystals and may be used on a support, such as an alumina support, if desired. The mole ratio of air to methanol in this feed is maintained between about 0.95 and 1.29 and the space velocity is usually maintained in a range of from 100,000 to 500,000 reciprocal hours, preferably 100,000 to 300,000 reciprocal hours. If desired steam may be added as a diluent, the amount supplied in the feed mix being usually in the range of from 5 to 10% by weight based on the methanol in the feed.

The effluent gases from the primary converter are cooled to below 300°C. by heat exchange, mixed with secondary air, and then passed through a secondary converter containing silver catalyst in the form of silver crystals as specified above and reacted at an adiabatic temperature in the range of from 600°C. to about 700°C. The space velocity maintained in the secondary converter is preferably maintained in the range as stated before, namely 250,000 to 600,000 reciprocal hours. The important feature is that the space velocity be in excess of 250,000 reciprocal hours. The amount of secondary air added to the gases entering the secondary converter is such that the mole ratio of total air, i.e., air in the original feed plus air added between stages to methanol is in a range of from about 1.90 to 2.4.

It is found to be of definite advantage in the process of the invention to control the depth of the catalyst bed regardless of bed diameter. The average depth of silver crystals should not exceed 4 inches. Preferably the average bed depth will be held between 0.5 to 1.5 inches.

With regard to the space velocity used in the secondary converter, the particular choice within the preferred range of from 250,000 to 600,000 reciprocal hours will depend in large part on the geometry and size of the catalyst bed used for the process.

The effluent gases from the secondary converter are cooled by heat exchange to below 300°C. and then passed into an absorber to collect the condensed product and separate out the non-condensible gases which are vented to the atmosphere.

In a typical embodiment the following type and arrangement of equipment can be utilized to execute the process of the invention.

Methanol is passed through a vaporizer and the expanding volume of the methanol vapor forces it onto a preheater. Air is forced by a blower through another preheater to mix with the hot methanol vapor prior to the entry of both streams into a primary oxidizer.

Gases emerging from oxidizer pass through a cooler before being butted up with secondary air supplied from the blower through another preheater. The resulting gaseous mixture then passes into the secondary oxidizer where the final conversion to formaldehyde takes place.

The effluent gas emerging from secondary oxidizer passes through a cooler before passing into the base of absorber column. A stream of water may be introduced at the top of the absorber column in order to adjust the formaldehyde concentration in the aqueous formaldehyde product which is removed from the bottom of column. The non-condensible gases entering absorber are vented at the top of the column to the atmosphere.

The unexpected advantage of the process of the invention is that at comparable conversions to formaldehyde much lower amounts of unconverted methanol are obtained with the use of silver crystals as a catalyst and space velocities above 250,000 reciprocal hours in the second stage converter. In the prior art two-stage oxidation schemes, in order to reduce the undesirable amounts of methanol more severe operating conditions are required which in turn causes an increase in the formation of undesirable byproducts.

This invention will be better understood by reference to the following illustrative examples wherein all percentages shown are by weight unless otherwise designated.

EXAMPLE 1

A mixture of air and methanol vapor in a mole ratio of 1.06 is preheated to 105°C., passed through a primary converter containing an insulated silver gauze bed of 154 sq. in. area by 1 inch depth at 1,000 pounds per hour, and thereafter cooled from the reaction temperature of 565°C. to 193°C. by a water cooled heat exchanger. Additional air is heated to 180°C. and added at the rate of 420 pounds per hour to the primary converter effluent gases to make a total air/methanol mole ratio of 2.00. This total mixture is then passed to a secondary converter containing 154 sq. in. area by 0.75 in. depth insulated bed of 20 to 30 mesh size electrolytically prepared silver crystals, and reacted at 625°C. The space velocity in this secondary converter is maintained at 449,000 reciprocal hours. The effluent gases are then promptly cooled to 190°C. by a water cooled heat exchanger. The cooled gas is then passed into an absorber to deliver an aqueous 60% formaldehyde solution product with less than 2% methanol by weight. The mole conversion from methanol to formaldehyde is 85.2%, the mole conversion from methanol to byproducts (as carbon dioxide, carbon monoxide, methane, and formic acid), is 12.0%, and the leakage is 2.8 moles percent methanol.

EXAMPLE 2

1200 lbs. per hour of feed mix at an air/methanol weight ratio of 1.01/1 is fed into a primary bed of silver gauze at 110°C. preheat temperature, reacted at 570°C. temperature, and cooled to 157°C. This primary feed mix contains 579 lbs. per hour air, 573 lbs. per hour methanol and 48 lbs. per hour steam. Approximately 63.0% of the methanol is converted to formaldehyde and 4.5% converted to carbon dioxide byproduct. The leakage of unreacted methanol is 32.5% or 186 lbs. per hour. The oxygen in the primary feed is completely combusted in the primary reaction. The effluent reaction gases are butted up with 500 lbs. per hour secondary air to a total air/methanol weight ratio of 1.88. The secondary feed is passed through a secondary converter containing a fixed bed of 193 troy ounces of electrolytically prepared silver crystals, 99.9% purity. This bed is 14 inches diameter and approximately 1½ inches depth with 8 to 16 mesh U.S. screen size particles. The secondary feed is reacted at 650°C. following an adiabatic temperature rise from 148°C. at a space velocity of 269,000 reciprocal hours. The effluent gases are immediately cooled to 204°C. in a shell and tube heat exchanger and passed into an absorber where the non-condensible gases are separated and vented to atmosphere and an aqueous solution of 61.1% formaldehyde and 1.7% methanol collected from the bottom. The formic acid in the solution is 150 ppm. The total conversion of methanol to formaldehyde is 83.55% and to carbon dioxide byproduct 14.5%. Leakage of unreacted methanol is 2.11%. The analysis of the off-gas vented from the absorber is 7.0% $CO_2$, 0.0% $O_2$, 0.1% CO, 18.2% $H_2$, and 0.1% $CH_4$.

EXAMPLE 3

A feed of 1200 lbs. per hour, composed of 593 lbs./hr. air, 558 lbs./hr. methanol and 50 lbs./steam at 1.06 primary air/methanol weight ratio, is preheated at 110°C. and reacted after an adiabatic temperature rise to 588°C., in a primary converter containing a bed of 50 sheets of silver gauze. The primary effluent gases are cooled to 169°C. in a shell and tube heat exchanger. Conversion in the primary reactor is 65.07% methanol to formaldehyde and 4.39% methanol to carbon dioxide. The methanol leakage is 30.54%. The primary effluent gases are butted up with 495 lbs. per hour secondary air, the total air/methanol weight ratio being 1.95. The secondary feed is preheated to 153°C. and reacted after an adiabatic temperature rise to 650°C. in a fixed bed reactor having 129 tr. oz. of 20 to 30 U.S. screen mesh size silver crystals and 64 tr. oz. of 30 to 40 U.S. screen mesh size silver crystals, both of electrolytic grade 99.9% purity. The depth of the catalyst bed in the secondary reactor is ¾ inch. The space velocity is maintained at 536,000 reciprocal hours.

The total conversion of methanol if 84.4% to formaldehyde, 15.1% to carbon dioxide byproduct and 0.5% leakage of unreacted methanol. After separation of condensibles in an absorber, the solution strength of the absorber bottom effluent is 61.1% formaldehyde and 1.0% methanol. The vented absorbed off gas is analyzed at 6.3 $CO_2$, 0.2% $O_2$, 0.1% CO, 0.1% $CH_4$ and 16.8% $H_2$.

It is claimed:

1. A two-stage process for the catalytic oxidation of methanol to formaldehyde comprising
   a. passing a vapor mixture of methanol and air, wherein the air to methanol mole ratio is in the range of from 0.95 to 1.29, into a primary oxidizer containing a silver catalyst at a space velocity of from 100,000 to 500,000 reciprocal hours whereby oxidation of methanol to formaldehyde occurs at an adiabatic temperature in a range of from 575° to 650°C.;
   b. cooling the effluent gases from said primary oxidizer to a temperature below 300°C.;
   c. admixing additional air with said cool gases so that the total air to methanol on a mole basis for the process is in the range of from 1.90 to 2.40;
   d. passing the resulting gaseous mixture into a secondary oxidizer at a space velocity of 250,000 to 600,000 reciprocal hours, said secondary oxidizer containing a catalyst bed having an average depth of from 0.5 to 1.5 inches of silver crystals having a size range of 8 to 40 screen mesh whereby further oxidation of methanol to formaldehyde occurs in an adiabatic temperature range of from 600° to 700°C.;
   e. cooling the effluent gases from said secondary oxidizer to a temperature below 300°C.; and
   f. passing said cooled gases resulting from step (e) to an absorber and collecting the condensed liquid product formed therein.

2. The process of claim 1 wherein the catalyst bed in said secondary oxidizer contains crystals having a particle size range of 20 to 30 screen mesh.

3. A two-stage process for the catalytic oxidation of methanol to formaldehyde comprising
   a. passing a vapor mixture of methanol, steam and air, wherein the air to methanol mole ratio is in the range of from 0.95 to 1.29, into a primary oxidizer containing a silver catalyst at a space velocity of from 100,000 to 300,000 reciprocal hours whereby oxidation of methanol to formaldehyde occurs at an adiabatic temperature at a range of from 575° to 650°C.;
b. cooling the effluent gases from said primary oxidizer to a temperature below 300°C.;
c. admixing additional air with said cool gases so that the total air to methanol on a mole basis for the process is in a range of from 1.90 to 2.40;
d. passing the resulting gaseous mixture into a secondary oxidizer at a space velocity of 250,000 to 600,000 reciprocal hours, said secondary oxidizer containing a catalyst bed having an average depth of from 0.5 to 1.5 inches of silver crystals having a size range of 20 to 30 screen mesh whereby further oxidation of methanol to formaldehyde occurs in an adiabatic temperature range of from 600° to 700°C.;
e. cooling the effluent gases from said secondary oxidizer to a temperature below 300°C.; and
f. passing said cooled gases resulting from step (e) to an absorber and collecting the condensed liquid product formed therein.

* * * * *